United States Patent

Thompson

[11] Patent Number: 5,879,891
[45] Date of Patent: Mar. 9, 1999

[54] TRANSFORMATION OF SACCHAROMYCES CEREVISIAE BY ELECTROPORATION

[75] Inventor: John R. Thompson, Scotch Plains, N.J.

[73] Assignee: Merck & Co., Inc., Rahway, N.J.

[21] Appl. No.: 932,004

[22] Filed: Sep. 17, 1997

[51] Int. Cl.$^6$ ....................................................... C12Q 1/68
[52] U.S. Cl. ............................................ 435/6; 435/172.3
[58] Field of Search ...................................... 435/6, 172.3

[56] References Cited

U.S. PATENT DOCUMENTS 5,593,859  1/1997  Prockop et al. ........................ 435/69.1

OTHER PUBLICATIONS

J. of Genl. Microbiology, vol. 132, pp. 3089–3093 (1986) by B. Brzobohaty, et al.

Biochemical & Biophysical Research Communications, vol. 164, No. 3, pp. 1157–1164 (1989), by J. R. Simon, et al.

Nucleic Acids Research, vol. 18, No. 5, p. 1313 (1989), by E. L. Rech, et al.

FEBS Letters, vol. 182, No. 1, pp. 90–94 (1985), by I. Karube, et al.

Appl. Microbiol Biotechnol. vol. 21, pp. 336–339 (1985), by H. Hashimoto, et al.

Methods of Enzymology, vol. 194, No. 12, pp. 182–187 (1991), by D. M. Becker, et al.

Applied & Environmental Microbiology, vol. 55, No. 9, pp. 2241–2246 (1989), by E. Delorme.

*Primary Examiner*—James Ketter
*Attorney, Agent, or Firm*—Elliott Korsen; Mark R. Daniel

[57] ABSTRACT

There is disclosed a procedure for DNA-mediated transformation of *Saccharomyces cerevisiae* by electroporation utilizing lithium acetate and dithiothreitol to weaken cell wall structure resulting in increased transformation efficiency.

6 Claims, No Drawings

TRANSFORMATION OF SACCHAROMYCES CEREVISIAE BY ELECTROPORATION

FIELD OF THE INVENTION

The present invention relates to a procedure for DNA-mediated transformation of Saccharomyces cerevisiae by electroporation. More particularly, the invention relates to the treatment of the host strain with lithium acetate and dithiothreitol (DTT) in order to weaken cell wall structure and increase the efficiency of transformation.

BACKGROUND OF THE INVENTION

Electroporation has become the preferred method for gene transfer due to its ease and efficiency of operation in comparison to alternate techniques. To date, electroporation has been utilized to transform a wide variety of cell types including mammalian cells, plant protoplasts, bacteria, fungi and yeast. The technique involves subjecting cells to a high voltage electric field, which results in the temporary formation of pores in the membrane, thereby allowing exogenous DNA to enter the cells. For example, laboratory strains of the yeast Saccharomyces cerevisiae have been transformed through electroporation with either self-replicating plasmids or by integration of linearized plasmid DNA in the host genome.

Yeast provide an attractive alternative to prokaryotes as host organisms. They can be used for large scale fermentations and are adaptable to continuous fermentation processing. In addition, they are not susceptible to phage infection and generally require only semi-sterile conditions. Conveniently, these cells may be immobilized for the production of metabolites and enzymes.

A number of yeast strains have been used as host organisms for recombinant gene expression.

References describing transformation of S. cerevisiae by electroporation include Hashimoto et al., Appl Microbiol Biotechnol (1985) 21:336–339; Karube et al., FEBS (1985) 182:90–94; Rech et al., Nucleic Acids Research (1989) 18:1313; Simon and McEntee, Biochemical and Biophysical Research Commmunications (1989) 164:1157–1164; Dolorme, E., Appl. Environ. Microbiol (1989) 55: 2242–2246; and Becker and Guarente, Methods in Enzymology (1991) 194: 182–187. Transformation of S. cerevisiae with alkali cations or thiol compounds is described by Ito et al., J. Biol. Chem. (1984) 48: 163–168; Brzobohaty and Kovac, J. of General Microbiology (1986) 132:3089–3093.

SUMMARY OF THE INVENTION

The present invention relates to a process for the transformation of Saccharomyces cerevisiae for use as a preclinical research tool. The invention also relates to the use of the transformed host to develop screens to detect new drugs.

DETAILED DESCRIPTION OF THE INVENTION

The present invention relates to a novel process for the transformation of Saccharomyces cerevisiae by electroporation. More particularly, the invention relates to the treatment of the host strain with lithium acetate and DTT in order to weaken cell wall structure and effect an optimized yield of transformants.

The first aspect of the invention relates to the process which comprises (1) pre-treating the host strain with lithium acetate/DTT; (2) adding plasmid DNA containing a selectable transformation marker to the treated host strain; (3) introducing said DNA construct into the host strain by application of an electrical pulse to form transformed cells; and (4) selecting said transformed cells, in this case, by their ability to grow in medium selecting for the plasmid encoded marker.

A second aspect of the invention relates to the use of the transformed host strains as a preclinical tool.

A third aspect of the invention relates to the introduction of other genes into Saccharomyces that would be antifungal targets. For example, it is contemplated that introduction of genes from pathogenic organisms into S. Cerevisiae to develop Saccharomyces-based screens for inhibitors of gene products derived from pathogenic fungi is within the scope of the invention.

The transformation methodology described here represents an improvement over an established electroporation protocol in order to achieve a higher efficiency of transformation. Achieving the highest possible efficiency of transformation is of particular advantage in circumstances where large numbers of transformants are required or transforming DNA is in limited supply. For example, a mutant host strain is often transformed with a plasmid-based genomic library as a means to isolate and identify the wild-type gene corresponding to the mutant allele. Typically, tens of thousands of transformants are required in such an experiment and the library DNA is often in limited supply. Such DNA libraries can, in principal, be amplified to produce more DNA, however, this is undesirable because each round of amplification results in a degradation of the representation of the library and lessens the chance that the gene of interest will be found. Thus, any improvement in transformation efficiency reduces consumption of precious and often irreplaceable DNA preparations. Further, while many wild-type laboratory strains transform well with established methods, very often introduction of a desired mutation into a strain results in a concomitant reduction of the strain's transformation efficiency. In some cases, mutant strains can be completely refractory to transformation by established methods. The transformation procedure described here is particularly advantageous in these situations.

Various procedures for transforming Saccharomyces cerevisiae are currently in use. The original spheroplast method remains one of the most efficient methods in terms of yield of transformants per microgram of DNA. However, preparation of spheroplast competent cells is time consuming, relies on carefully controlled enzymatic digestion of the cell wall by crude preparations of glucanase and requires plating of transformants embedded in soft agar. Moreover, transformation by the spheroplast method often results in cell fusion events and the resulting ploidy variation can complicate downstream genetic analyses. These disadvantages of the spheroplast method provided the impetus for workers in the field to develop alternative methods.

A procedure based on chemical treatment with alkali metals such as lithium acetate was developed by Ito et al (J. Biol. Chem. (1984) 48: 163–168). This method requires fewer manipulations than the spheroplast protocol and allows direct spread plating of transformants on the surface of agar plates. Chen et al. improved on the lithium treatment protocol by the addition of DTT, a chemical known to release mannoproteins from the yeast cell wall (Chen et al., Curr Genet (1992) 21:83–84). Variations of the lithium treatment method are still in widespread use because of their relative simplicity compared to the spheroplast method. However, the best optimized lithium treatment protocols are less efficient than spheroplasting method.

Several electroporative methods for transformation of Saccharomyces have been developed. The first electroporation protocols, while even less laborious than the lithium treatment protocols, provided relatively low yields of transformants (Hashimoto et al., Appl Microbiol Biotechnol (1985) 21:336–339; Karube et al., FEBS (1985) 182:90–94; Rech et al., Nucleic Acids Research (1989) 18:1313; Simon and McEntee, Biochemical and Biophysical Research Commmunications (1989) 164:1157–1164; Dolorme, E., Appl. Environ. Microbiol (1989) 55: 2242–2246). However, Becker and Guarente published an optimized protocol for electroporation that resulted in a transformation efficiency greater than the original spheroplast methodology while preserving the simplified preparation procedures common to the electroporative methods. The electroporation protocol of Becker and Gaurente involves extensive washing of cells to reduce ionic strength and electroporation of cells as a concentrated cell suspension in an osmotically supported low ionic strength solution. Our protocol introduces a short pretreatment with lithium acetate and DTT prior to this washing procedure. This simple modification results in a 5–10 fold increase in transformation efficiency.

The transformed S. cerevisiae can be used to study mode of action of antifungals as well as to evaluate potential resistant mechanisms. They can also be used for developing screens to detect new drug candidates. Additionally, they can be used for molecular manipulation of S. cerevisiae for gene cloning and gene disruption experiments.

The protocol is generalizable to work with any yeast auxotrophic or antibiotic resistance marker (e.g. -his, -leu, -ura, -ade, -trp or G418 resistance).

The following examples are provided to illustrate the invention but are not to be construed as limiting the scope of the invention.

Materials and Methods

Strains and DNA were isolated and handled by standard procedures [J. Sambrook, E. F. Fritsch, and T. Maniatis, "Molecular Cloning, A Laboratory Manual", second edition, Cold Spring Harbor Laboratory Press, Cold Spring Harbor, N.Y. (1989)], referred to as Maniatis. Media recipes and many of the procedures for working with S. cerevisiae are described in M. D. Rose, F. Winston, and P. Hieter, "Methods in Yeast Genetics: a Laboratory Course Manual", Cold Spring Harbor Laboratory Press, Cold Spring Harbor, N.Y. (1990), referred to as MYG.

Two host strains of Saccharomyces cerevisiae were selected to demonstrate the improved efficiency of the new electroporation protocol. Strain YPH98 is a wild-type strain that generally transforms with high efficiency and possesses several common auxotrophic markers (MATα ura3–52 lys2–801, ade2–101 trp1-Δ1 leu2-Δ1). A second strain, R812–18 is a spontaneous mutant of YPH98 selected for resistance to an antifungal agent. R812–18 also shows reduced transformation efficiency with respect to its wild-type parent, YPH98. The plasmid used in this example is pRS316 and is a centromeric autonomously replicating plasmid carrying a selectable URA3 marker (Sikorski and Hieter, Genetics (1989) 122:19–27).

EXAMPLE 1

Preparation of Electrocompetent cells 100 ml of YPAD medium were inoculated with a colony or 0.1 ml of a saturated starter culture. The culture was grown overnight at 28°–30° C. and cells were harvested when an $OD_{600}$ of 1.0–1.5 was obtained. Cells were harvested by centrifugation at 3000 RPM and suspended in 25 ml of a LiAc/DTT/TE solution consisting of 100 mM lithium acetate, 10 mM DTT, 10 mM Tris pH 7.5, and 1 mM EDTA (filter sterilized). Cells were incubated in the LiAc/DTT/TE solution for 1 hour on ice with occasional gentle mixing. The cells were harvested at 3000 RPM and washed twice with 50 ml of ice cold sterile water and once with 10 ml ice cold 1M sorbitol. The final cell pellet was suspended in a volume of 1M sorbitol equal to the wet weight of the cell pellet thus forming a 50% suspension of cells (typically ~0.2–0.4 ml).

It is believed that the DTT can be used in a range of about 10 mM to about 100 mM.

Electroporation of Whole Cells

10–100 ng of DNA in 1–5 μl of water or TE buffer was placed in a sterile screw cap microfuge tube. Electrocompetent cells (50 μl) were added and mixed. The mixture was transferred to a pre-chilled 0.2 mm Biorad electroporation cuvette. Electroporation was performed with a BioRad Gene Pulser instrument set at 1500v, 25 μF, and 200 Ω. The resulting time constants reported by the instrument were 4.5–5.0 ms. The electroporated samples were immediately diluted with 1 ml of ice cold sterile 1M Sorbitol and returned to ice. Aliquots of the transformation mix were either plated directly or diluted as needed with additional 1M sorbitol and spread onto the appropriate selective medium. The transformants were incubated 3–5 days at 28°–30° C. to allow colony formation.

Comparison Of Transformation Efficiency With And Without Lithium Acetate/Dtt Pretreatment Electrocompetent YPH98 and R812–18 cells were prepared as outlined above. To illustrate the benefit of the lithium acetate/DTT incubation, two batches of cells were prepared from each strain and the lithium acetate/DTT pretreatment was omitted for one of the batches. 50 μl aliquots of each electrocompetent cell preparation were electroporated as described above after mixing with 100 ng of pRS316 DNA in 5 μl of TE buffer (10 mM Tris, 1 mM EDTA pH 7.5). The electroporated cells were serial diluted, plated on synthetic complete medium lacking uracil and incubated 4 days at 30° C. to allow colony formation. The resulting transformants were counted on dilution plates that yield between 90 and 400 colonies per plate. The results, expressed as transformants per microgram of DNA, are tabulated below.

| Strain | Pretreatment | Transformation Frequency | Relative Increase |
| --- | --- | --- | --- |
| YPH98 | none | $1.25 \times 10^5$ | 1.0 |
| YPH98 | Lithium Acetate/DTT | $1.41 \times 10^6$ | 11.3 |
| R812-18 | none | $1.62 \times 10^4$ | 1.0 |
| R812-18 | Lithium Acetate/DTT | $9.25 \times 10^4$ | 5.7 |

The relative increase listed reflects the increase in transformation efficiency directly attributable to the lithium acetate/

DTT pretreatment. While the absolute transformation efficiency of the mutant strain R812–18 is about 8-fold lower than its wild-type parent, both strains showed a similar relative increase in efficiency as a result of the lithium acetate/DTT pretreatment.

EXAMPLE 2

Independent Contribution Of Lithium Acetate And DTT To Enhanced Transformation Efficiency This example serves to illustrate the contribution of both lithium acetate and DTT to the overall increase in transformation efficiency. Experimental procedures were identical to Example 1 with the exception that pretreatment during competent cell preparation was varied to consist of no pretreatment, pretreatment with lithium acetate only (100 mM lithium acetate, 10 mM Tris, 1 mM EDTA pH 7.5), pretreatment with DTT only (10 mM DTT, 1 mM EDTA pH 7.5), and standard pretreatment with lithium acetate/DTT (0.1M lithium acetate, 10 mM DTT, 1 mM EDTA pH 7.5). A culture of YPH98 was harvested separated into 4 aliquots and electrocompetent cells prepared with each of the 4 described pretreatments. The plasmid used for transformation in this experiment is YEPlac195 (Gietz and Sugino, Gene (1988) 74:527–534). The plasmid is a multi-copy yeast plasmid bearing a 2 $\mu$M origin of replication and the URA3 gene as a selectable marker.

Cells (40 $\mu$l) from each of the four different pretreatments were electroporated with 100 ng of YEPlac195 using the same electroporation conditions as Example 1. The electroporated samples were serially diluted, 0.1 ml aliquots spread plated on synthetic complete medium lacking uracil and incubated 4 days at 30° C. Colony counts were collected from dilution plates with between 100–250 colonies and used to calculate the transformation efficiencies. The results are tabulated below.

Because lithium acetate and DTT treatments have been shown to stimulate DNA uptake in the absence of an electrical pulse, we tested the dependence of our transformation protocol on the electrical pulse. A sample of lithium acetate/DTT pretreated electrocompetent cells was mixed with DNA but not subjected to an electrical pulse before plating on selective medium. This sample yielded zero transformants (<1 transformant/10 ng DNA) and illustrates the importance of the electrical pulse to the success of the procedure. The lack of even a low frequency of transformants from the lithium acetate/DTT treated cells in the absence of a pulse is not unexpected however. The non-electroporative lithium acetate methodology for transforming yeast relies on a treatment of the competent cell/DNA mixture with concentrated polyethylene glycol solution to induce DNA uptake and generally calls for the addition of a 10 to 100 fold greater amount of DNA to the reaction. No polyethylene glycol is involved in our procedure.

| Pretreatment | Transformation Frequency | Relative Increase |
|---|---|---|
| None | $2.38 \times 10^4$ | 1X |
| Lithium Acetate | $9.30 \times 10^4$ | 3.9X |
| DTT | $9.3 \times 10^4$ | 3.9X |
| Lithium Acetate + DTT | $2.8 \times 10^5$ | 11.8X |

Examination of the results shows that pretreatment with either lithium acetate or DTT alone showed some increase in efficiency. However, the combination of both lithium acetate and DTT in the pretreatment results in the highest transformation efficiency conferring roughly an order of magnitude increase over no pretreatment.

What is claimed is:

1. A method for transforming *Saccharomyces cerevisiae* comprising the steps of
   a) treating the host strain with lithium acetate/dithiothreitol;
   b) adding plasmid DNA containing a selectable transformation marker to the treated host strain;
   c) introducing said DNA construct into the host strain by application of an electrical pulse to form transformed cells; and
   d) selecting said transformed cells.

2. The method of claim 1 wherein the host strain is an auxotrophic mutant.

3. The method of claim 1 wherein the selectable transformation marker is the appropriate wild-type gene capable of complementing the said auxotrophy or an antibiotic resistance marker capable of conferring antibiotic resistance to the transformed cells.

4. The method of claim 1 wherein the transformed cells are selected by their ability to grow in selective medium lacking the appropriate nutrient or containing the appropriate antibiotic.

5. The method of claim 1 wherein about 100 mM of the lithium acetate is employed.

6. The method of claim 1 wherein about 10 to about 100 mM of the dithiothreitol is employed.

* * * * *